(12) United States Patent
Wandke et al.

(10) Patent No.: US 9,005,188 B2
(45) Date of Patent: Apr. 14, 2015

(54) ELECTRODE ARRANGEMENT FOR A DIELECTRIC BARRIER DISCHARGE PLASMA TREATMENT AND METHOD FOR PLASMA TREATMENT OF A SURFACE

(75) Inventors: Dirk Wandke, Heilbad Heiligenstadt (DE); Maximilian Segl, Duderstadt (DE); Leonhard Trutwig, Duderstadt (DE)

(73) Assignee: CINOGY GmbH, Duderstadt (DE)

( * ) Notice: Subject to any disclaimer, the term of this patent is extended or adjusted under 35 U.S.C. 154(b) by 388 days.

(21) Appl. No.: 13/517,437

(22) PCT Filed: Dec. 22, 2010

(86) PCT No.: PCT/DE2010/001513
§ 371 (c)(1),
(2), (4) Date: Jun. 20, 2012

(87) PCT Pub. No.: WO2011/076193
PCT Pub. Date: Jun. 30, 2011

(65) Prior Publication Data
US 2012/0259270 A1    Oct. 11, 2012

(30) Foreign Application Priority Data

Dec. 24, 2009    (DE) .......................... 10 2009 060 627

(51) Int. Cl.
*A61B 18/04*    (2006.01)
*A61N 1/44*    (2006.01)
(Continued)

(52) U.S. Cl.
CPC ................ *A61N 1/44* (2013.01); *A61N 1/0408* (2013.01); *A61N 1/0476* (2013.01); *A61N 1/0492* (2013.01); *A61N 1/40* (2013.01); *H05H 1/24* (2013.01)

(58) Field of Classification Search
CPC ......... A61N 1/40; A61N 1/44; A61N 1/0408; A61N 1/0492; A61N 1/408; H05H 1/24
USPC ....................................................... 606/32, 40
See application file for complete search history.

(56) References Cited

U.S. PATENT DOCUMENTS 8,136,481 B2 *   3/2012   Viol et al. ................. 118/723 E
2002/0005395 A1    1/2002   Yanobe
(Continued)

FOREIGN PATENT DOCUMENTS

DE           38 31 964 A1    6/1989
DE          103 44 489 A1    4/2005
(Continued)

*Primary Examiner* — Catherine Voorhees
(74) *Attorney, Agent, or Firm* — Whitham Curtis Christofferson & Cook, PC

(57) ABSTRACT

The invention relates to an electrode arrangement for a dielectric barrier discharge plasma treatment of an irregularly three-dimensionally shaped surface of an electrically conducting body used as a counter electrode, comprising a planar electrode (1) and a dielectric (2, 3), which is designed to be arranged at a defined distance from the surface to be treated in order to form a cold plasma, wherein said arrangement can be produced in a simple manner and can be reliably designed in the use thereof in that the dielectric (2, 3) is formed by a flexible planar material, which is provided with a structure (4) on the side of the flexible planar material facing the surface to be treated in order to form air guiding areas (7) when the dielectric (2, 3) lies on the surface to be treated, and in that the planar electrode is flexible and Is fastened to the dielectric (2, 3) in such a way that a layer (2) of the dielectric (2, 3) shields the electrode (1) from the surface to be treated.

12 Claims, 2 Drawing Sheets

(51) Int. Cl.
*A61N 1/04* (2006.01)
*A61N 1/40* (2006.01)
*H05H 1/24* (2006.01)

(56) References Cited

U.S. PATENT DOCUMENTS

| | | | |
|---|---|---|---|
| 2008/0183167 A1 | 7/2008 | Britva et al. | |
| 2009/0054896 A1* | 2/2009 | Fridman et al. | 606/49 |
| 2010/0145253 A1* | 6/2010 | Gutsol et al. | 604/20 |
| 2012/0107896 A1* | 5/2012 | Wandke et al. | 435/173.6 |
| 2013/0090542 A1* | 4/2013 | Kipke et al. | 600/377 |

FOREIGN PATENT DOCUMENTS

| | | |
|---|---|---|
| DE | 10 2007 030 915 A1 | 1/2009 |
| DE | 2007 030 915 A1 | 1/2009 |
| DE | 102008030913 A1 | 1/2010 |
| DE | 197 17 698 A1 | 6/2012 |
| EP | 1 933 605 A1 | 6/2008 |
| WO | 2007/067924 A2 | 6/2007 |
| WO | 2009/098662 A1 | 8/2009 |
| WO | 2010/006676 A1 | 1/2010 |
| WO | 01/69644 A1 | 3/2011 |

* cited by examiner

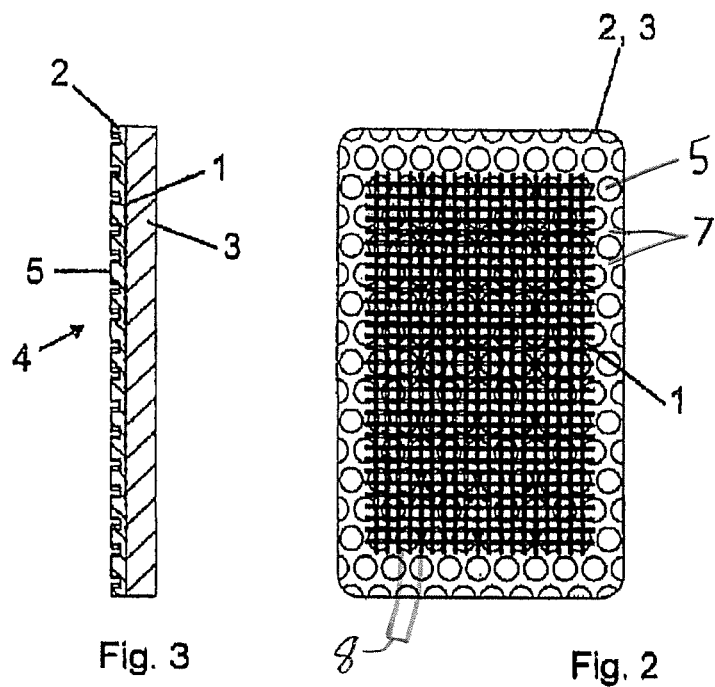
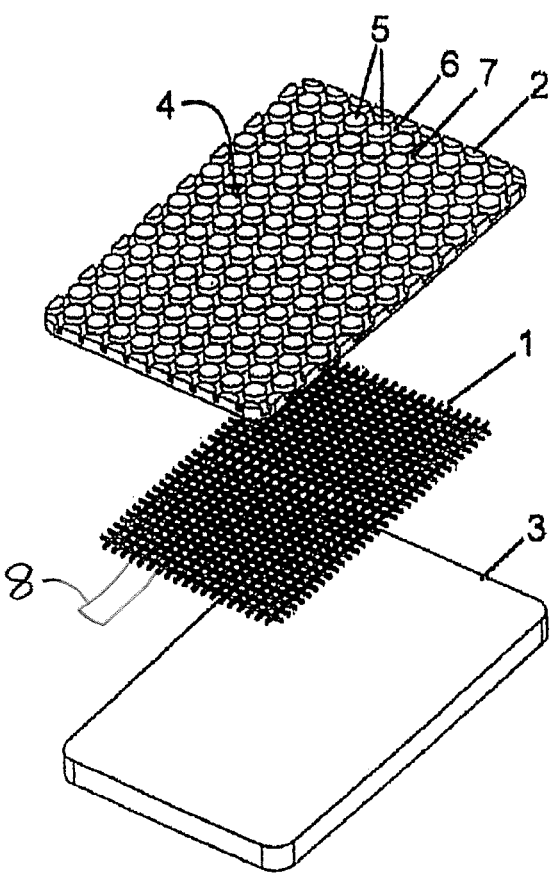
Fig. 3
Fig. 2
Fig. 1

ELECTRODE ARRANGEMENT FOR A DIELECTRIC BARRIER DISCHARGE PLASMA TREATMENT AND METHOD FOR PLASMA TREATMENT OF A SURFACE

FIELD OF THE INVENTION

The invention relates to an electrode arrangement for a dielectric barrier discharge plasma treatment of an irregularly three-dimensionally shaped surface of an electrically conducting body, which surface is used as a counter electrode, comprising a planar electrode and a dielectric, which is designed to be arranged at a defined distance from the surface to be treated in order to form a cold plasma.

The invention also relates to a method for plasma treatment of a surface with such an electrode arrangement.

BACKGROUND OF THE INVENTION

Dielectric barrier discharge plasma treatments are used in numerous applications. DE 195 32 105 C2 discloses the treatment of the surface of three-dimensional workpieces, for example their activation or cleaning. By means of a so-called barrier discharge it is possible to reduce a layer of oil down to minimum oil coatings. In doing so however, it is essential that a uniform treatment of the surface takes place. This requires a homogeneous structure of the plasma, wherein the idea is that the plasma discharges take place in thin filaments spaced apart from one another. This is problematic in the case of irregularly three-dimensionally shaped surfaces. In DE 195 32 105 C2 it is therefore provided that a negative mold of the surface of the workpiece is constructed with the dielectric, which thus consists of a malleable plastic, for example one that can be pressed or cold-drawn. It is also provided that an intermediate layer is used, so that the dielectric layer can be formed with the intermediate layer directly on the surface of the workpiece. The intermediate layer is then removed in order to ensure an intermediate space is provided between the dielectric and the electrode, in which the plasma can form. On its side facing away from the surface to be treated, the dielectric is coated with a conductive material, to which the required high voltage can be applied in the form of an alternating voltage.

From DE 10 2007 030 915 A1 it is known to form hollow fibers from a dielectric material, which are provided internally with a metallic conductive coating, so that the hollow fiber forms a dielectric with an inner shielded electrode, which together with the surface of a conductive body, serving as a counter-electrode, can form a plasma field. In addition, a fabric is formed with the hollow fibers, which can be placed in two-dimensional contact with an irregular surface, in particular a skin surface of a human body. This results in the advantage of an electrode arrangement which is adaptable to the irregular topology of the skin surface for carrying out a plasma treatment. A disadvantage associated with this method, however, is the high manufacturing costs of constructing the hollow fibers forming the fabric, which must comprise a flexible electrode in their inner cavity in order to ensure the necessary flexibility of the electrode fabric for adapting to the surface of the skin.

SUMMARY OF THE INVENTION

The problem addressed by the present invention therefore is to create an electrode arrangement with which a secure dielectric barrier plasma treatment of the surface of an irregularly three-dimensionally shaped body, in particular the surface of the skin of an organism, is possible, and which is easier and cheaper to produce.

This problem is solved according to the invention with an electrode arrangement of the above-mentioned type by the fact that the dielectric is formed by a flexible planar material which is provided with a structure on the side of said material facing the surface to be treated, in order to form air guiding areas when the dielectric lies on the surface to be treated, and that the planar electrode is flexible and is fastened to the dielectric in such a way that a layer of the dielectric shields the electrodes from the surface to be treated.

As the raw material for the electrode arrangement according to the invention, therefore, a smooth planar dielectric is preferably used, which on its surface facing away from the surface to be treated carries a smooth flat electrode, such that a flexible sheet is formed which, due to its flexibility, is adaptable to the contour of the surface, even if this is three-dimensionally shaped and in particular has an irregular three-dimensional topography. Essential to the invention is the fact that the dielectric forms a continuous layer, with which the electrode is shielded from the surface to be treated. In addition, the dielectric forms a structure in the direction of the surface to be treated, which contains areas in which air can be supplied and replaced, in order to cause the emergence of the cold plasma in these areas, with which the surface, in particular the skin surface of a human or animal body, is treated. The treatment of the skin surface can be a therapeutic treatment. A cosmetic treatment of the surface is preferred, however, by means of which these cosmetic materials can be better absorbed, whereby cosmetic treatments, such as wrinkle removals or pore reductions etc., are possible in an efficient manner. Another effective treatment can be obtained by implementing the electrode arrangement as a sock liner. This results in a bactericidal and fungicidal effect on the skin of the foot, wherein the dielectric can rest on the skin of the foot either directly or through a stocking, and in particular on the sole of the foot.

The planar electrode is preferably embedded in the dielectric. This can be effected on the back of the layer of dielectric, which shields the electrode from the surface to be treated. It is also possible, however, to fully embed the planar electrode in the dielectric. In all cases the planar electrode can be brought into contact with a terminal which is brought out of the dielectric.

The electrode is preferably formed by a flexible wire mesh, because this is simple and cost-effective to produce for a flexible electrode.

In a preferred embodiment, the structure of the dielectric is formed integrally with the layer of dielectric which shields the electrode from the surface to be treated. The structuring then defines the depth of the areas in which air can be located to form the plasma when the dielectric is placed directly onto the surface, for example skin. If the dielectric is formed of a suitable plastic, for example thermoplastic polyethylene, the desired structure can be applied during the molding of the flat dielectric.

It is also possible, however, to connect the structure to the layer of dielectric as a separately formed layer. In this case the structure can also be formed from fine fibers, and be, for example, a fabric, which increases the air-conducting areas where possible and allows a more consistent structure of the plasma to be obtained.

In a design of the structure based on projecting elevations, which is simpler from a production engineering point of view, air-permeable intermediate spaces are provided in which the plasma can form. The elevations can preferably be implemented in a circular-cylindrical, conical or frustoconical form. In addition, the elevations preferably have a height between 0.5 and 10 mm, preferably between 1 and 8 mm, and further preferably between 2 and 3 mm.

The invention will be explained in more detail below, based on an exemplary embodiment illustrated in the drawing. In the figures:

BRIEF DESCRIPTION OF THE DRAWINGS

FIG. 1 shows the parts of an arrangement according to the invention in an exploded view;

FIG. 2 shows a plan view of the front of the assembled electrode arrangement according to FIG. 1;

FIG. 3 shows a longitudinal section through the electrode arrangement according to FIG. 2;

DETAILED DESCRIPTION OF THE INVENTION

Figure 5:
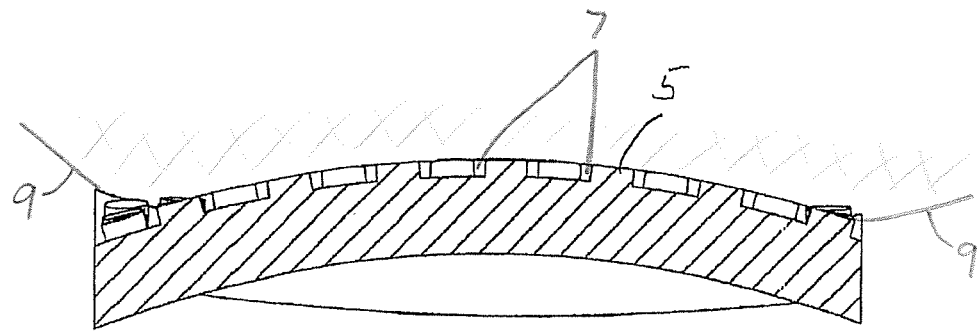
FIG. 5 shows a longitudinal section through the electrode arrangement along the line V-V in FIG. 4.

FIG. 1 illustrates that the electrode arrangement according to the invention has an electrode 1, implemented as a metal electrode array which in its initial state is flat and flexible. The electrode is arranged between a front layer 2 made of a dielectric material and a rear-facing layer 3 made of a dielectric material. The two dielectric layers 2, 3 have a flat and planar construction in their initial state, and project beyond the electrode 1 at all four side edges, so that the electrode 1 is embedded in the dielectric formed by the two layers 2, 3 on all sides. To this end, the layers 2, 3 are connected to each other, preferably two-dimensionally. The connection can be made, for example, by adhesive bonding or welding. Of course, releasable connections can also be realized using external connection means, but at higher cost. The electrode 1 embedded in the dielectric can be contacted with a terminal (8) projecting out of the dielectric.

The front layer 2 of the dielectric is provided with a structured surface 4 on the side facing away from the electrode 1. In the exemplary embodiment illustrated, the structured surface is formed by protruding elevations 5, separated from one another by a distance 6, so that the structured surface 4 has numerous interconnected air guiding areas 7 in which air can flow when the electrode arrangement with the elevations 5 of its front layer 2 rests in contact with a surface to be processed, for example on the skin of a living organism.

FIG. 2 illustrates that, viewed from above, the electrode 1 ends at a distance from the side edges of the layers 2, 3, the layers 2, 3 being preferably formed so that they are equal in size.

The longitudinal section of FIG. 3 illustrates the embedding of the electrode 1 between the layers 2, 3, and the elevations 5 of the structured surface 4 of the front layer 2, which shields the electrode 1 from the surface to be processed.

Figure 4:
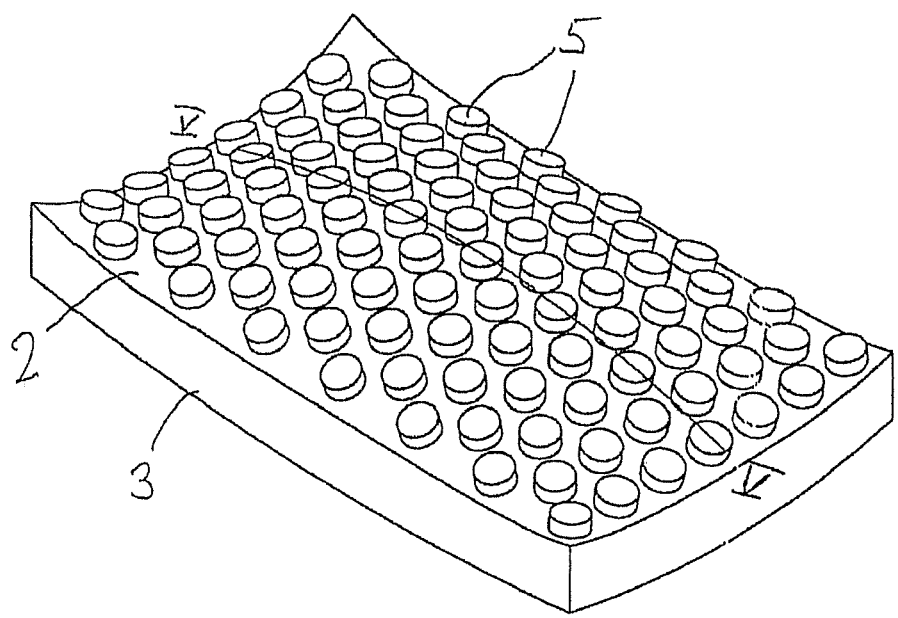
FIG. 4 shows a perspective view of an electrode arrangement adapted to a three-dimensionally shaped surface.

FIG. 4 shows a perspective view of the electrode arrangement in accordance with FIG. 1, wherein the two layers 2, 3 of the dielectric are no longer separated from each other, for example because they are joined together by a flat welding process. The dielectric 2, 3 thus formed is flexible, because the layers 2, 3, on the one hand, and the electrode 1 embedded therein, on the other, are flexible. Accordingly, the electrode arrangement can be adapted to match the shape of a three-dimensionally shaped surface, as is indicated schematically in FIG. 4. The surface to be treated (9) is shown in FIG. 5. It is apparent that a central curvature, which is convex when viewed from above, gradually becomes a concave curvature towards the diagonally opposite ends. This illustrates the adaptive capacity of the electrode arrangement, even to irregular curvatures of the surface to be treated.

The longitudinal section along the line V-V of FIG. 4, shown in FIG. 5, illustrates the central convex curvature, and allows a concave curvature rising toward the rear to be identified, in particular at the left-hand end.

It is readily apparent that the electrode arrangement according to the invention is extremely easy to produce, and in a simple manner allows a two-dimensional treatment of even an irregularly curved surface, and in particular a skin surface.

FIGS. 4 and 5 show the fusion of the two dielectric layers 2, 3 into a single component, in which the electrode 1 is enclosed.

It is readily possible also to implement the structured surface 4 as a separate planar element which is connected to the layer 2 shielding the electrode 1. For example, the structured surface can be formed in this manner by means of a flat flexible textile fabric or plastic fabric, which, although unsuitable as a shielding layer 2, being a structured surface 4 it is however suitable for implementing air guiding areas in which the plasma required for the treatment is formed by the high alternating voltage applied.

It is also conceivable, for a number of applications, to apply the electrode 1 only on the back face of the dielectric layer 2. In general though, it will be useful to cover the electrode 1 with an insulating layer, to prevent unwanted voltage discharges, for example onto an operator, occurring on the back face of the shielding layer 2. Therefore, the embedding of the electrode 1 in the dielectric 2, 3 represents a preferred embodiment.

The exemplary embodiment shown is based on smooth flat layers 2, 3 in the initial state and a smooth flat electrode 1. For applications intended, for example, in particular for convex curved surfaces, it can also be practical to use flat layers 2, 3 pre-formed with a convex curvature, and a correspondingly preformed flat electrode 1. The same applies to other types of pre-forming which facilitates the adaptation to the surfaces to be treated, wherein the flexibility of the electrode arrangement is preserved in each case and enables a precise adaptation to the surface.

The invention claimed is:

1. An electrode arrangement for a dielectric barrier discharge plasma treatment of an irregularly three-dimensionally shaped surface of an electrically conducting body, which surface is used as a counter electrode, comprising:
    a planar electrode;
    a dielectric which is formed by a flexible planar material which is provided with a structured surface on a side of said material facing a surface to be treated,
        wherein the structured surface comprises a plurality of spaced apart projections which extend from a base of said side of said material which faces the surface to be treated to an elevation spaced apart from said base so as to form air guiding areas when the dielectric lies on the surface to be treated in order to form a cold plasma in said areas, and
        wherein the planar electrode is flexible and fastened to the dielectric, wherein the dielectric forms a continuous layer in such a way that the continuous layer shields the planar electrode from the surface to be treated.

2. The electrode arrangement as claimed in claim 1,
further comprising a terminal which is brought out of the dielectric, wherein the planar electrode is embedded in the dielectric and is configured to be brought into contact with the terminal.

3. The electrode arrangement as claimed in claim 2,
wherein the planar electrode is embedded in the dielectric on all sides.

4. The electrode arrangement as claimed in claim 1, wherein
the dielectric is designed to rest on the skin of a living organism.

5. The electrode arrangement as claimed in claim 1, wherein
the electrode is formed by a flexible wire mesh made of metal.

6. The electrode arrangement as claimed in claim 1, wherein
the electrode is formed of carbon fibers or carbon fiber mesh.

7. The electrode arrangement as claimed in claim 1, wherein
the structured surface of the dielectric is formed integrally in the continuous layer which shields the planar electrode from the surface to be treated.

8. The electrode arrangement as claimed in claim 1, wherein
the structured surface is a separately constructed layer and is connected to the continuous layer which shields the planar electrode from the surface to be treated.

9. The electrode arrangement as claimed in claim 1, wherein
said projections are generally flat topped.

10. The electrode arrangement as claimed in claim 9,
the projections are implemented in a circular-cylindrical, conical or frustroconical form.

11. A method for plasma treatment of a surface by means of an electrode arrangement for a dielectric barrier discharge plasma treatment of a surface of an electrically conducting body, which surface is used as a counter electrode, comprising:
a planar electrode;
a dielectric which is formed by a flexible planar material which is provided with a structured surface on a side of said material facing the surface to be treated, which forms air guiding areas when the dielectric lies on the surface to be treated in order to form a cold plasma in said areas, and
wherein the planar electrode is flexible and fastened to the dielectric wherein the dielectric forms a continuous layer in such a way that the continuous layer shields the planar electrode from the surface to be treated, comprising the steps of:
placing the planar electrode arrangement with the structure of the dielectric formed in the direction of the surface to be treated on the surface to be treated;
adapting the planar electrode arrangement to the contour of the surface to be treated; and
plasma treating the surface to be treated.

12. The method as claimed in claim 11,
wherein in the placing step the electrode arrangement is placed on an irregularly three-dimensionally shaped surface of said surface to be treated.

* * * * *